(12) United States Patent
Müller et al.

(10) Patent No.: US 7,803,606 B2
(45) Date of Patent: Sep. 28, 2010

(54) METHOD FOR THE PRODUCTION OF FLAVOR-ACTIVE TERPENES

(75) Inventors: Martin Müller, Freising (DE); Kerstin Dirlam, Freising (DE); Hans Henning Wenk, Freising (DE); Ralf G. Berger, Hannover (DE); Ulrich Krings, Landesbergen (DE); Rüdiger Kaspera, Oldenburg (DE)

(73) Assignee: Maxens GmbH, Trostberg (DE)

(*) Notice: Subject to any disclaimer, the term of this patent is extended or adjusted under 35 U.S.C. 154(b) by 574 days.

(21) Appl. No.: 10/587,706

(22) PCT Filed: Feb. 10, 2005

(86) PCT No.: PCT/EP2005/001346

§ 371 (c)(1),
(2), (4) Date: Jul. 28, 2006

(87) PCT Pub. No.: WO2005/078110

PCT Pub. Date: Aug. 25, 2005

(65) Prior Publication Data

US 2007/0172934 A1    Jul. 26, 2007

(30) Foreign Application Priority Data

Feb. 11, 2004   (DE) .................. 10 2004 006 825

(51) Int. Cl.
*C12P 41/00* (2006.01)
(52) U.S. Cl. .................................... 435/280
(58) Field of Classification Search ............ None
See application file for complete search history.

(56) References Cited

FOREIGN PATENT DOCUMENTS

EP    1 424 071 A1    3/2002

OTHER PUBLICATIONS

ATCC Filamentous Fungi, 19$^{th}$ Edition, p. 227, 1996.*
Kaspera et al., "Stereospecific allylic oxidation of limonenes: a route to pure S-(+)- and R-(−)-carvones", Flavour Research at the Dawn of the Twenty-First Century, Proceedings of the Weurman Flavor Research Symposium, 10$^{th}$, Beaune, France Jun. 25-28, 2002 (2003), 397-400., Eds. LeQere et al.*
Sundari, S. Krishna et al., "Freeze-Drying Vegetative Mycelium of *Laccaria fraterna* and Its Subseequent Regeneration," *Biotechnology Techniques*, vol. 13, pp. 491-495 (1999).
Croan, Suki C., "Lyophilization of Hyph-Forming Tropical Wood-Inhabiting Basidiomycotina," *Mycologia*, vol. 92(4), pp. 810-817 (2000).
Onken, J. et al., "Effects of R-(+)-Limonene on Submerged Cultrues of the Terpene Transforming Basidiomycete *Pleurotus sapidus*," *Journal of Biotechnology*, vol. 69, pp. 163-168 (1999).
Taubert, J. et al., "A Comparative Study on The Disintegration of Filamentous Fungi," *Jounral of Microbiological Methods*, vol. 42, pp. 225-232 (2000).
Kaspera, Rüdiger et al., "Bioconversion of (+)-Valencene in Submerged Cultures of the Ascomycete *Chaetomium globosum*," *Appl. Microbiol. Biotechnolo.* vol. 67, pp. 477-483 (2005).

* cited by examiner

*Primary Examiner*—Sandra Saucier
(74) *Attorney, Agent, or Firm*—Ping Wang; Morris, Manning & Martin, LLP

(57) ABSTRACT

Disclosed is a method for producing flavor-active terpenes from terpene hydrocarbons. According to said method, a lyophilized mycel which is first rehydrated and is then mixed with the substrate is used preferably in a submerged culture in the framework of selective biotransformation with the aid of microorganisms. The inventive method, which can be carried out especially in an enantioselective, stereoselective, and/or regioselective manner, makes it possible to obtain terpenoid alcohols, epoxides, aldehydes, ketones, polyalcohols, carbonyls, and carbonyl alcohols with the aid of *fusarium, pleutorus, penicillium*, and *chaetomium* species, the obtained substances being isolated particularly from cellular components. Said method should be carried out above all in a stirred tank, surface reactor, or fixed bed reactor while preferably taking place in a two-phase system with reduced carbon source moieties. The obtained flavor-active terpenes are used as flavors and fragrances preferably in the food, cosmetic, and pharmaceutical industry.

21 Claims, No Drawings

METHOD FOR THE PRODUCTION OF FLAVOR-ACTIVE TERPENES

The present invention relates to a method for the production of flavor-active terpenes using a selective biotransformation.

Flavors and perfumes have an important role in today's society. Odor-active substances are used in a large number of everyday products, such as perfumes, cosmetics, foods, pharmaceutical products and household products. For example, 15% of all foods on the market are flavored with additives. Obtaining flavorings by means of extraction or distillation even nowadays still takes place from a wide variety of plant parts (fruits, leaves, seeds, roots, etc.). Extracts or even isolated compounds are traded as high-value products (for example, in the perfume industry as "essence absolue").

The great need, which continues to increase, for flavorings can no longer be met by natural extracts alone, for which reason up to about 80% of the production of flavorings takes place by way of chemical synthesis. The synthesis stages are often complex, not very specific and therefore, according to the Flavor Law (in the version dated 18 Jun. 2001), the products can only be declared "nature-identical" in terms of food law, but not "natural". According to the Flavor Law, natural flavors can be produced "... by enzymatic or microbiological methods from starting substances of plant or animal origin". Therefore, the development of biotechnological processes for producing natural flavorings is a sensible alternative. The production of flavors by means of biotransformations, i.e. the biocatalytic transformation of starting components into synthetic products by, for example, microbial metabolization, accordingly also gives the flavorings produced the "natural" quality, whereby, primarily with consumers, they obtain a decisively higher degree of acceptance.

Terpene hydrocarbons and their oxidation products, the terpenoids, form an important group of flavorings. As widespread natural substances their sensorial or pharmacological effects have long been known. Mono- and sesquiterpenes are used as products of secondary metabolism in the plant and animal worlds as attractants or, owing to their toxological effect, as protection against pests. They also act as cues and phytohormones. Thus, for example, terpenes absorbed and metabolized with vegetable nourishment are used by insects as sociohormones or communication pheromones. Olfactorily-active terpenes are often distinguished by extraordinarily low odor thresholds and as what are known as "character impact compounds" form the flavor-forming ingredient of a specific flavor, for example rosenoxide for the scent of geraniums with an odor threshold of 0.5 µg kg$^{-1}$ as a typical orange flavor.

The natural precursors of terpenoids are expedient as the starting compounds for the production thereof. These mono- and sesquiterpene hydrocarbons, which are of less interest, are separated from the high-value terpenoids and occur as "waste" on the ton scale. Thus the monoterpene R-(+)-limonene is produced as waste material from orange oil processing in quantities of more than 100,000 t per year and is traded at a reasonable price. With a content of more than 90% it occurs as the main component of the orange peel oil and accumulates during rectification. Owing to their virtually unlimited availability and structural similarity, terpene hydrocarbons form the ideal basic materials for production of the corresponding oxidation products by chemical or biocatalytic synthesis.

A virtually unlimited number of biocatalysts, such as bacteria, yeasts, fungi, and plant cells, can be used for a terpene biotransformation, wherein fungi have proven to be particularly active biocatalysts. According to current knowledge, more than 100,000 types are known from the field of Mycobionta (fungi), of which some organisms have provided the economy with access to production of a range of important compounds, such as antibiotics, vitamins and organic acids. In biotechnology a distinction is made here between de novo production, in other words direct excretion as the metabolic product by vital cell systems, and biotransformation with which structurally similar precursors are transformed into the desired end products by targeted functional reactions. In addition to direct production a large number of microorganisms are capable of breaking down and metabolizing xenobiotic and macromolecular substrates.

Higher fungi in particular, such as basidiomycetes, have a large number of oxidatively acting enzymes for wood disintegration (for example laccases, peroxidases) owing to their natural habitat. The approx. 30,000 species of basidiomycetes currently known are therefore particularly expedient for oxidative biotransformations of terpene hydrocarbons. For example, the repellent α-pinene excreted by plants can be detoxified by microbial oxidation. The advantage of fungi over lower organisms, such as bacteria, is the significantly more diverse provision of redoxenzymes with high oxidation potential, and this enables them to oxidize xenobiotic substances in particular.

Owing to their structural complexity the chemical total synthesis of sesquiterpenoids presents the flavorings industry with extraordinary difficulties, however. In the simplest manner synthesis can be carried out by the functionalisation of natural precursors, wherein chemical synthesis stages have proven to be sparsely selective, however.

From the known problems of the prior art the object was thus posed for the present invention of providing a method for the production of flavor-active terpenes from terpene hydrocarbons, which method is carried out within the framework of a selective biotransformation and using microorganisms of the ascomycetes, basidiomycetes and deuteromycetes classes. In this case the primary objective was the provision of a method which is to be carried out in a simple and economical manner, in the process uses the selective properties of enzymatic processes and, starting from easily accessible and inexpensive starting substances, leads to high-value products with pronounced purity, which products are suitable in particular for food technology applications.

This object was achieved using a corresponding method, wherein a lyophilized mycel is used which is firstly rehydrated and then mixed with the substrate.

Surprisingly it has been found that owing to the method step of perforation of the mycel cells by lyphophilization measures, enzyme systems in whole cell cultures may be used, wherein the culture medium does not have to be mixed with any additional activators. According to the object posed, not only are the desired flavor-active terpenes obtained in outstanding qualities with this method, but it is also possible to produce the desired compounds in an enantioselective, a stereoselective and/or regioselective manner by choosing suitable microorganisms and to obtain them by simple measures, in terms of process engineering, from the reaction medium. In particular the enantioselective production of monoterpenoids by biotransformation was previously possible to only a very limited degree owing to the lack of suitable organisms and enzymes. Owing to the previous difficulties, as are known from chemical processes, and also from variations in the methods of biotransformation, the advantages of the method according to the invention were not to be expected in this development.

As already indicated, an advantage, essential to the invention, of the present method can be seen in the fact that a lyophilized mycel is used. In order to be able to utilize the advantages of this method feature even more, the present invention provides that a mycel is used, of which the cells have been additionally permeated by ultrasonic treatment and/or extrusion.

The cellular biocatalysts used can thus be pre-treated before their use in the actual transformation reaction in such a way that the starting compounds initially penetrate the cell wall and can subsequently diffuse into the cell membranes. The drawbacks of the cell membrane as an osmotic barrier are therefore overcome and the inhibition of the biotransformation, conventionally connected therewith and previously known, as takes place for example in the form of a deceleration of the influx of substrates and the efflux of products, can be reduced or completely avoided. As a result of the perforation measures the substrate exchange can be much accelerated as a disturbance to the membrane integrity is brought about, primarily by the lyophilization, wherein, however, the enzyme systems contained therein are intact but at the same time are more easily accessible.

It has proven to be particularly expedient if the proposed method is carried out in a submerged culture. A further advantage of the method according to the invention can be seen in that the biotransformation can be carried out in an enantioselective, a stereoselective or a regioselective manner.

The choice of suitable microorganisms plays a significant role in the success of the method according to the invention. In this connection the present invention takes into account a variant in which representatives of *Fusarium, Pleurotus, Penicillium* and *Chaetomium* are used as the biocatalysts. *Fusarium proliferatum, Pleurotus sapidus, Penicillium citrinum* and *Chaetomium globosum* have proven to be particularly suitable.

With respect to the flavor-active terpenes to be obtained, mono- and sesquiterpenes are preferred by the present invention as the starting terpene hydrocarbons, wherein limonene and in particular R-(+)-limonene or S-(−)-limonene, and pinene, valencene, farnesene, thymol and dimethyl allyl alcohol are to be regarded as particularly suitable.

In specific cases it can be advantageous to carry out an enzyme induction in the lyophilized mycel before the actual biotransformation, for which the addition of substrate has proven to be suitable. After their rehydration in a buffer, the lyophilisates of the mycel are conventionally mixed with a specific quantity of substrate, whereby the fungal culture is adapted and an induction of enzymes, which are suitable for terpene oxidation, is achieved. The starting terpene hydrocarbon is actually added between a few hours to two days after in this case.

As a further preferred variant the present invention provides that the biotransformation is carried out in a two-phase system comprising water and an organic phase, wherein n-decane in particular has proven itself as a suitable phase. Biotransformation is particularly preferably carried out without the addition of co-solvents, and the invention also takes this into account.

A further advantage of the method according to the invention consists in that the biotransformation reaction can be carried out in a medium which contains a reduced quantity M of the otherwise conventional carbon source, such as glucose, whereby a higher biotransformation of the given substrate takes place. M is preferably <50 gL$^{-1}$, more preferably <25 gL$^{-1}$, and most preferably <10 gL$^{-1}$.

Biotransformation reactions are conventionally carried out in aqueous systems, wherein the use of organic solvents increases the availability of lipophilic substrates if the distribution equilibrium of starting material and substrates/products is disadvantageous in aqueous medium. As already described, a suitable solvent was determined in the form of a two-phase system, wherein n-decane constitutes the organic phase. If, on the other hand, n-decane is used as the co-solvent this can lead to activity inhibition of the enzymes, depending on the mycel used, for which reason the present invention also recommends dispensing with co-solvents.

With respect to the end products, the method according to the invention provides that these be isolated from cellular components or cell fractions of the mycel. Lipophilic substances are conventionally enriched by more than 90% in the mycel and in particular in the cell wall and membrane fractions here. An imperceptibly small fraction of approx. just 5% is found in the aqueous medium.

As an optimum supply of oxygen is needed for successful biotransformation, it is recommended that the proposed method is carried out in appropriate devices, such as stirred tank, surface and fixed bed reactors, which the present invention recommends in particular. The metabolic path of the terpenes in the respective microorganism plays an important role in numerous biotransformations. It is known here that co-oxidation of the terpene substrate plays a role for some microorganisms, without further oxidation and metabolization taking place. Metabolization of terpenes as the carbon source is not necessary, in particular if nutrient-rich media are used. On the other hand, terpene hydrocarbons can be used as the sole carbon source and metabolized via a β-oxidation. With respect to the carbon sources present in the culture medium in particular, it has been shown to be advantageous for the present method that a glucose content G with G≦0.5% is sufficient for cultivating transformation-active biomasses. It was also confirmed that the organic main components of the culture medium, namely carbon and nitrogen, have a decisive influence on the transformation yield. It has again proven to be expedient if a low-carbon medium, as already discussed, is used in order to thus increase the oxidation product content, wherein a more far reaching mineralization of the target product is successfully prevented.

The shaking apparatus, also already discussed, in particular has a further important role as oxygen is an essential co-substrate of the oxidation of terpene hydrocarbons, and for which reason primarily aerobic fungi, such as ascomycetes, require on an obligatory basis sufficient quantities of oxygen for maintaining vital processes and for optimal biomass production. Thus, it must be ensured that there is sufficient oxygen available during cultivation, and this can be done with the stirred tank, surface and fixed bed reactors discussed. In addition, there is also a surface enlargement of the shaking culture, accompanied by an increased exchange of gas and improved mass transfer coefficients.

The present method has proven particularly suitable for obtaining terpenoid alcohols, epoxides, aldehydes, ketones, multiple alcohols, carbonyls and carbonyl alcohols as the end products. Particularly preferred in this connection are piperitone, isopiperitone, isopiperitenol, isopiperitenone, perillaaldehyde, carvone, carveol, linalool, linalool oxide, terpineol and nootkatol and nootkatone.

Finally, the present invention also takes into account method variants with which flavor-active terpenes may be produced in a targeted manner. Thus, it is recommended in particular to firstly biotransform in an enantioselective manner R-(+)-limonene to cis-(+)-carveol and S-(−)-limonene to trans-(−)-carveol, for which specific *Fusarium* types in particular have proven to be suitable as biocatalysts. The trans- (−)-carveol thus obtained can subsequently be transformed to R-(−)-carvone, wherein *Pleurotus* spec. strains should be used in this case.

The present invention also includes the biotransformation of bicyclic sesquiterpenes to β-nootkatol and subsequently to nootkatone, for which *Chaetomium* species are recommended.

In addition to the described method and its diverse variants, the present invention also takes into account the use of the terpenes obtainable therewith as odorants, flavors and flavorings, wherein their use in the food, cosmetics and pharmaceutical industries should be regarded as preferred.

The described method allows refinement of specific terpene hydrocarbons, such as limonene, valencene and famesene, to high-value flavor-active compounds, such as carvone, nootkatone and 7-hydroxy famesene by a microbial biotransformation. By choosing suitable fungi cultures, and in particular applying the lyophilized mycels obtained therefrom, it is possible to obtain the desired flavor-active terpenes in larger quantities and very good quality in an economically advantageous manner, wherein the biocatalytic conduction of the reaction as a whole can be carried out in submerged culture in suitable devices in a simple manner.

The following examples illustrate the advantages of the claimed method.

EXAMPLES

Mycelia which were cultivated in submerged cultures at 24° C. and 150 rpm, were used as biocatalysts for the following examples.

After 3 to 7 days' growth time 10 mL of homogenized medium were transferred from these precultures into 200 mL SNLH medium and cultivated at 24° C. and 150 rpm. To adapt the culture 20 µL of the respective terpene were then added after 3 to 5 days' growth time. The cell mass was then separated by centrifuging (2,000 g, 10 min), washed with 0.9% sodium chloride solution and cryotransferred using liquid nitrogen. Freeze drying or lyophilization (system: Finaqua Lyovac GT2) was carried out at ambient temperature and at $2 \times 10^{-5}$ bar for one to four day(s) (depending on culture).

Transformation Conditions:

For rehydration of the freeze-dried cell mass a lyophilisate which was reduced to small pieces was incubated in transformation medium (for example MOPS buffer, 4-[N-morpholino] butane sulphonic acid, yeast culture medium according to Sprecher and Hansen [1982]) for 1 to 24 h. The terpene hydrocarbon (1 to 300 mM) was added directly or by using solvents. The terpenoid formation was determined by taking continuous aliquot specimens. The terpenoids were obtained by solvent extraction. The identification of the compounds took place by means of GC-MS via authentic standards, quantification via GC-FID and the internal standards used.

Example 1

For transformation of limonene 50 mg *Pleurotus sapidus* mycel was placed in 1.5 mL MOPS buffer (0.1 M; pH 7.0) and the dried cell mass was rehydrated for one hour at 200 rpm and 24° C. For producing carvone 41 mM limonene were directly applied to the rehydrated culture. The reaction took place for 24 h at 150 rpm and 24° C. After addition of the internal standard (for example camphor for limonene transformation) samples were extracted with 2 mL azeotropic pentane/ether mixture, centrifuged and dried over night with $Na_2SO_4$.

The invention claimed is:

1. A method for producing oxidized flavor-active terpenes from terpene hydrocarbons by means of a selective biotransformation using microorganisms of the ascomycetes, basidiomycetes and deuteromycetes classes, comprising:

(a) perforating mycelium by lyphophilization measures and permeating mycelium by ultrasonic treatment and/or extrusion, wherein the permeating step may be performed before or after the perforating step, (b) rehydrating the perforated and permeated mycelium, (c) mixing the rehydrated mycelium from step (b) with the substrate, and (d) recovering the oxidized flavor-active terpene.

2. The method as claimed in claim 1, wherein the biotransformation is carried out in a submerged culture.

3. The method as claimed in claim 1, wherein the biotransformation is carried out in an enantioselective, a stereoselective and/or a regioselective manner.

4. The method as claimed in claim 1, wherein representatives of *Fusarium, Pleurotus, Penicillium* and *Chaetomium* are used as the microorganisms.

5. The method as claimed in claim 4, wherein *Fusarium proliferatus, Pleurotus sapidus, Penicillium citrinum* and *Chaetomium globosum* are used as the microorganisms.

6. The method as claimed in claim 1, wherein mono- and sesquiterpenes are used as the terpene hydrocarbons.

7. The method as claimed in claim 1 wherein limonene, pinene, valencene, farnesene, thymol and dimethyl allyl alcohol are used as the terpene hydrocarbons.

8. The method as claimed in claim 7, wherein R-(+) limonene or S-(−) limonene are used as the terpene hydrocarbons.

9. The method as claimed in claim 1, wherein before the biotransformation an enzyme induction is carried out in the mycelium prior to lyophilization by an addition of substrate.

10. The method as claimed in claim 1, wherein the biotransformation is carried out in a two-phase system.

11. The method as claimed in claim 10, wherein the biotransformation is carried out in a two-phase system without co-solvents.

12. The method as claimed in claim 1, wherein the biotransformation is carried out in a medium with a reduced quantity or carbon source in an amount $<50 \text{ gL}^{-1}$.

13. The method as claimed in claim 1, wherein the reaction is carried out in a stirred tank, surface or fixed bed reactor.

14. The method as claimed in claim 1, wherein terpenoid alcohols, epoxides, aldehydes, ketones, multiple alcohols, carbonyls and carbonyl alcohols are obtained as the flavor-active terpenes.

15. The method as claimed in claim 14, wherein piperitone, isopiperitone, isopiperitenol, isopiperitenone, perillaaldehyde, carvone, carveol, linalool, linalool oxide, terpineol and nootkatol and nootkatone are obtained.

16. The method as claimed in claim 1, wherein the biotransformation products are isolated from cellular compartments or fractions.

17. The method as claimed in claim 1, wherein firstly R-(+)-limonene is biotransformed in an enantioselective manner to cis-(+)-carveol and S-(−)-limonene is biotransformed in an enantioselective manner to trans-(−)-carveol and subsequently trans-(+)-carveol to R-(−)-carvone.

18. The method as claimed in claim 17, wherein the enantioselective biotransformation of R-(+)-limonene to cis-(+)-carveol is carried out with *Fusarium* species as the biocatalyst.

19. The method as claimed in claim 17, wherein the enantioselective transformation or trans-(−)-carveol to R-(−)-carvon is carried out with species of the genus *Pleurotus* as the biocatalyst.

20. The method as claimed in claim 1, wherein bicyclic sesquiterpenes are transformed to β-nootkatol and subsequently to nootkatone.

21. The method as claimed in claim 20, wherein the transformation of bicyclic sesquiterpenes to β-nootkatol and subsequently to nootkatone is carried out with *Chaetomium* species.

* * * * *